United States Patent [19]

Weiss

[11] Patent Number: 4,675,446
[45] Date of Patent: Jun. 23, 1987

[54] PROCESS FOR THE PREPARATION OF TERTIARY PHOSPHINE OXIDES

[75] Inventor: Erwin Weiss, Hofheim am Taunus, Fed. Rep. of Germany

[73] Assignee: Hoechst Aktiengesellschaft, Frankfurt am Main, Fed. Rep. of Germany

[21] Appl. No.: 756,323

[22] Filed: Jul. 18, 1985

[30] Foreign Application Priority Data

Jul. 20, 1984 [DE] Fed. Rep. of Germany ....... 3426721

[51] Int. Cl.$^4$ ............................................... C07F 9/53
[52] U.S. Cl. ..................................................... 568/14
[58] Field of Search .......................................... 568/14

[56] References Cited

U.S. PATENT DOCUMENTS 3,053,900 9/1962 Harwood et al. .................... 568/14
4,511,738 4/1985 Tokuyama et al. ................... 568/14

FOREIGN PATENT DOCUMENTS 1268619 5/1968 Fed. Rep. of Germany ........ 568/14

OTHER PUBLICATIONS

Kosolapoff et al., Organic Phosphorus Compounds, Wiley-Intersc. N.Y., vol. 14, pp. 25-26 (1972).
Hackh's Chemical Dictionary, McGraw Hill Book Co., Inc., N.Y. 3rd Edit., p. 633 (1944).
"Organische Phosphorverbindungen" (Organic Phosphorus Compounds) in Helvetica Chimica Acta 47, pp. 120-132 (1964).
A. M. Aguiar et al., in J. Org. Chem. 34 (1969), pp. 3349 to 3352.

Primary Examiner—Helen M. S. Sneed
Attorney, Agent, or Firm—Curtis, Morris & Safford

[57] ABSTRACT

Tertiary phosphine oxides are prepared by the oxidation of tertiary phosphine sulfides with $H_2O_2$ in a solvent composed of at least about 20% by weight, preferably at least about 50% by weight, of optionally halogenated, lower aliphatic carboxylic acids and/or their anhydrides; it is particularly preferred if the solvent is composed only of acetic acid.

The reaction products are end products and intermediates in a variety of areas such as, for example, the sectors of plant protection and polymers.

14 Claims, No Drawings

PROCESS FOR THE PREPARATION OF TERTIARY PHOSPHINE OXIDES

Tertiary phosphine oxides are compounds of the general formula $$R_3P=O$$

wherein R = identical or different organic radicals.

They are end products and intermediates in a variety of areas such as, for example, the sectors of plant protection and polymers.

A number of different methods are known for their preparation. Some of these methods are based on tertiary phosphine sulfides, which are converted to the corresponding phosphine oxides by means of an oxidative treatment. These methods are particularly appropriate in cases where the tertiary phosphine sulfides in question are readily available, so that the route via the sulfides to the phosphine oxides is more advantageous than other methods for the preparation of phosphine oxides.

The oxidative conversion of tertiary phosphine sulfides to the corresponding phosphine oxides can be carried out, for example, by means of $SOCl_2$, $KMnO_4$ or $HNO_3$; cf. the article by L. Maier entitled "Organische Phosphorverbindungen" ("Organic phosphorus compounds") in Helvetica Chimica Acta 47, pages 120–132, especially pages 124/125 (1964). In this literature reference, the following equations are given for oxidation with the said 3 reagents:

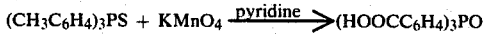

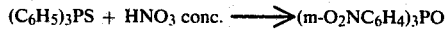

The disadvantages of the method with thionyl chloride, $SOCl_2$, are the strongly corrosive action of this reagent and the formation of the strong-smelling disulfur dichloride, $S_2Cl_2$, in this reaction.

Oxidation with $KMnO_4$ in pyridine gives only moderate yields of phosphine oxide, without exception, and—as can be seen from the above equation—is accompanied by oxidation of the alkyl group located on the aromatic nucleus to the carboxyl group in cases where aromatic phosphine sulfides alkylated on the nucleus are used.

In the reaction with concentrated nitric acid, nitration of the aromatic nuclei present takes place at the same time as the formation of phosphine oxide.

A more advantageous method for the oxidation of tertiary phosphine sulfides to the corresponding phosphine oxides is the hydrogen peroxide method published by A. M. Aguiar et al. in J. Org. Chem. 34 (1969), pages 3349 to 3352, especially the final paragraph of the right-hand column on page 3351. The method was described using the oxidation of dimethyl-1-butynylphosphine sulfide with an approximately 75% excess of $H_2O_2$ in methanol:

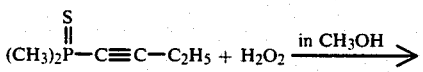

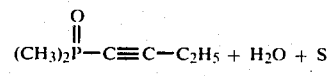

The yield of dimethyl-1-butynylphosphine oxide is said to have been 61% after the reaction mixture had stood for 2 days and been worked up in the appropriate manner. Because of the long reaction time, the only moderate yield and also the need to work up the hydrogen peroxide used in excess, this method is again unsatisfactory.

The problem was therefore to find an improved process for the conversion of tertiary phosphine sulfides to the corresponding phosphine oxides.

It was possible to solve this problem, according to the invention, by using optionally halogenated, lower aliphatic carboxylic acids and/or their anhydrides as the solvent or at least as a constituent of the solvent in the oxidation of tertiary phosphine sulfides with $H_2O_2$.

The invention therefore relates to a process for the preparation of tertiary phosphine oxides by means of an oxidative treatment of tertiary phosphine sulfides with $H_2O_2$ in a solvent; this process comprises using a solvent which is composed of at least about 20% by weight, preferably at least about 50% by weight, of optionally halogenated, lower aliphatic carboxylic acids and/or their anhydrides, the remainder being composed of other inert solvents miscible therewith. It is particularly preferred if the solvent used is composed only of optionally halogenated, aliphatic $C_1$–$C_6$-carboxylic acids and/or their anhydrides, especially acetic acid only.

The process takes place in short reaction times, without the formation of troublesome by-products, with quantitative or almost quantitative yields of the appropriate phosphine oxides. This is exceptionally surprising in view of the long reaction time and the only moderate yield in the case of oxidation with $H_2O_2$ in methanol (cf. A. M. Aguiar et al., loc. cit.) and also—as shown by our own experiments—the negative result of the treatment of tertiary phosphine sulfides with $H_2O_2$ in other solvents (acetonitrile, acetone etc.).

Suitable optionally halogen-substituted, lower aliphatic carboxylic acids are preferably aliphatic $C_1$–$C_6$-carboxylic acids which can be further substituted by one or more halogen atoms, preferably F and/or Cl. Examples of such carboxylic acids are: formic acid, acetic acid, propionic acid, monochloroacetic acid, monofluoroacetic acid, trifluoroacetic acid etc.

The carboxylic acids and their anhydrides can be used either individually or in mixtures with one another. They should make up at least about 20% by weight, preferably at least about 50% by weight, of the total solvent. It is particularly preferred if the solvent is composed only of these carboxylic acids and/or their anhydrides. It is very particularly preferred if the solvent is composed only of acetic acid (glacial acetic acid).

In cases where the solvent is not composed only of the said carboxylic acids and/or their anhydrides, the components of the mixture must be miscible with the carboxylic acids and/or their anhydrides; furthermore, of course, they must not undergo undesirable reactions with the hydrogen peroxide or the starting materials and end products of the reaction. Suitable examples of such components of the mixture are therefore water, lower ($C_1$–$C_6$)-alcohols such as methanol or ethanol, lower aliphatic halogenated hydrocarbons such as methylene chloride, 1,2-dichloroethane etc., aromatic hydrocarbons such as toluene or xylene, and aromatic chlorohydrocarbons such as chlorobenzene, fluorobenzene, etc.

Water and alcohols, as components of the mixture, are only useful when mixed with the abovementioned carboxylic acids, not with their anhydrides, because acids or esters form with the anhydrides. If the solvent is to be composed of the acids, they are advantageously used directly as such and not first produced from the anhydrides and water.

Of course, the lower the miscibility of the additional solvent constituents with the carboxylic acids and/or their anhydrides, the lower also is their possible proportion in the corresponding solvent mixture.

In principle, all possible compounds described as tertiary phosphine sulfides can be used as tertiary phosphine sulfides for the process. It is preferred to use phosphine sulfides of the formula

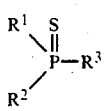

wherein $R^1$, $R^2$ and $R^3$ = independently of one another, $C_1$-$C_{12}$-alkyl, $C_6$-$C_{10}$-aryl and $C_6$-$C_{20}$-aralkyl groups optionally substituted by inert groups.

If the alkyl, aryl and aralkyl groups are substituted by inert groups, the substituents are preferably halogen atoms, especially only F and/or Cl atoms. Other preferred inert substituents for the aryl and aralkyl groups are alkyl radicals (preferably having up to 4 C atoms).

Examples of tertiary phosphine sulfides are: triphenylphosphine sulfide, diphenylmethylphosphine sulfide, dimethylphenylphosphine sulfide, tris(4-fluorophenyl)phosphine sulfide, bis(4-fluorophenyl)(2-fluorophenyl)phosphine sulfide, bis(4-fluorophenyl)phenylphosphine sulfide, (4-fluorophenyl)(2-fluorophenyl)phenylphosphine sulfide, diphenyl(4-fluorophenyl)phosphine sulfide, diphenyl(2-fluorophenyl)phosphine sulfide, bis(4-fluorophenyl)methylphosphine sulfide, (4-fluorophenyl)(2-fluorophenyl)methylphosphine sulfide, dimethyl(4-fluorophenyl)phosphine sulfide, bis(4-fluorophenyl)(4-methylphenyl)phosphine sulfide, bis(4-fluorophenyl)(2-methylphenyl)phosphine sulfide, (4-fluorophenyl)(2-fluorophenyl)(4-methylphenyl)phosphine sulfide, bis(4-methylphenyl)(4-fluorophenyl)phosphine sulfide, (4-fluorophenyl)(4-methylphenyl)(2-methylphenyl)phosphine sulfide, tris(4-chlorophenyl)phosphine sulfide, bis(4-chlorophenyl)(2-chlorophenyl)phosphine sulfide, bis(4-chlorophenyl)phenylphosphine sulfide, (4-chlorophenyl)(2-chlorophenyl)phenylphosphine sulfide, diphenyl(4-chlorophenyl)phosphine sulfide, bis(4-chlorophenyl)methylphosphine sulfide, (4-chlorophenyl)(2-chlorophenyl)methylphosphine sulfide, dimethyl(4-chlorophenyl)phosphine sulfide, (4-chlorophenyl)methylphenylphosphine sulfide, (4-fluorophenyl)(4-chlorophenyl)phenylphosphine sulfide, (4-fluorophenyl)(4-chlorophenyl)methylphosphine sulfide, (4-fluorophenyl)methylphenylphosphine sulfide, tris(4-methylphenyl)phosphine sulfide, bis(4-methylphenyl)(2-methylphenyl)phosphine sulfide, bis(4-methylphenyl)(3-methylphenyl)phosphine sulfide, bis(4-methylphenyl)phenylphosphine sulfide, (4-methylphenyl)(2-methylphenyl)phenylphosphine sulfide, (4-methylphenyl) (3-methylphenyl)phenylphosphine sulfide, diphenyl(4-methylphenyl)phosphine sulfide, diphenyl(3-methylphenyl)phosphine sulfide, diphenyl(2-methylphenyl)phosphine sulfide, bis(4-methylphenyl)methylphosphine sulfide, (4-methylphenyl) (2-methylphenyl)methylphosphine sulfide, (4-methylphenyl) (3-methylphenyl)methylphosphine sulfide, dimethyl(4-methylphenyl)phsophine sulfide, dimethyl(2-methylphenyl)phosphine sulfide and dimethyl(3-methylphenyl)phosphine sulfide.

Hydrogen peroxide can be used as an approximately 3 to 85% aqueous solution, advantageously in the commercially available form (approximately 30 to 35%). The hydrogen peroxide is preferably used in approximately the equimolar quantity based on the starting phosphine sulfide. A small excess of up to about 5% is advantageous; larger excesses are possible but no longer advantageous.

The phosphine sulfides are dissolved or suspended in the solvent. The ratio of phosphine sulfide:solvent can vary within wide limits. A weight ratio of approx. 1:(1-20) is advantageous. An aqueous solution of hydrogen peroxide is metered into the solution or suspension at temperatures generally of between about $-5°$ and $+100°$ C., preferably of between about $+40°$ and $+80°$ C. As the reaction is exothermic, cooling may be necessary. Accordingly, cold solutions or suspensions of phosphine sulfides must not be preheated in order to reach the desired reaction temperature; the desired temperature can preferably be reached using the heat of reaction itself.

The reaction mixture is worked up in a manner known per se by filtration of the cooled solution to remove the sulfur normally obtained in the elemental form.

On the one hand the very low solubility of elemental sulfur in carboxylic acids and/or their anhydrides, and on the other hand the good solubility of tertiary phosphine oxides in carboxylic acids and/or their anhydrides, even in the presence of the water unavoidably obtained in the course of the reaction, have a particularly favorable effect here.

After the solvent has been distilled off (preferably in vacuo), the phosphine oxides are obtained as the residue, usually initially as oily carboxylic acid adducts. The free phosphine oxides can easily be obtained in pure form by heating in vacuo or distillation. It is also possible to stir the carboxylic acid adducts in water and, if appropriate, cleave them by neutralization with bases. The free phosphine oxides precipitate from the aqueous, possibly alkaline solution and can be filtered off or—if they are liquid—separated off as a second phase.

Because the reaction is easy to carry out, the reaction times are short and the yields of phosphine oxide are high, the process represents a substantial advance in this area. Another advance worthy of mention is the fact that it is not necessary to use excess $H_2O_2$ (in contrast to the process of A. M. Aguiar et al., loc. cit.), which makes the reaction mixture considerably easier to work up.

The examples which follow are intended to illustrate the invention in greater detail. The examples (according to the invention) are followed by a few comparative examples, which shows that the oxidation of tertiary phosphine sulfides with $H_2O_2$ in solvents other than those to be used according to the invention does not take place or, if it does, the extent of reaction is far from satisfactory.

(A) EXAMPLES (ACCORDING TO THE INVENTION)

Example 1

18.16 g (50 mmol) of bis(4-chlorophenyl)phenylphosphine sulfide were dissolved in 50 ml of glacial acetic acid at 50° C., and 1.79 g (52.5mmol) of hydrogen peroxide (4.51 ml of a 35% aqueous solution) were added dropwise over a period of 15 minutes. Sulfur began to separate out after only a few drops. External cooling with ice ensured that the internal temperature did not exceed 70° C. The mixture was subsequently stirred for 30 minutes at 70° C. and cooled to room temperature, the sulfur was filtered off and the filtrate was evaporated at 100° C./20 mbar. The residue was suspended in 50 ml of water, and 2N NaOH was added until an alkaline reaction was obtained. Bis(4-chlorophenyl)phenylphosphine oxide was filtered off, rinsed with water and dried in vacuo at 100° C.

Yield: 16.9 g (97% of theory);
Melting point: 107° C.

Example 2

13.41 g (50 mmol) of bis(-fluorophenyl)methylphosphine sulfide were dissolved in 50 ml of glacial acetic acid, and 1.70 g (50 mmol) of hydrogen peroxide (4.3 ml of a 35% aqueous solution) were added dropwise over a period of 15 minutes. External cooling restricted the reaction temperature to 60° C. After 30 minutes at 60° C., the mixture was cooled to 20° C. and filtered and the filtrate was evaporated at 100° C./20 mbar. The residue was stirred in 75 ml of water, and 2N NaOH was added until an alkaline reaction was obtained. The product was filtered off, washed with water and dried at 100° C./20 mbar.

Yield: 12.0 g (95% of theory);
Melting point: 113°–114° C.

Example 3

13.41 g (50 mmol) of bis(4-fluorophenyl)methylphosphine sulfide were dissolved in 50 ml of glacial acid, and 1.70 g (50 mmol) of hydrogen peroxide (4.3 ml of a 35% aqueous solution) were added dropwise at 60° C. over a period of 15 minutes. After 30 minutes at 60° C., the mixture was cooled to 20° C., the sulfur was filtered off, the filtrate was evaporated and the residue was distilled using a kugelrohr at 0.1 mbar.

Yield: 12.2 g (97% of theory);
Melting point: 113°–114° C.

Example 4

The procedure was as in Example 2. 11.7 g (96% of theory) of bis(4-methylphenyl)methylphosphine oxide were obtained from 13.02 g (50 mmol) of bis(4-methylphenyl)methylphosphine sulfide and 1.70 g (50 mmol) of hydrogen peroxide (4.3 ml of a 35% solution).

Melting point: 146° C.

Example 5

The procedure was as in Example 2. 15.2 g (97% of theory) of bis(4-fluorophenyl)phenylphosphine oxide were obtained from 16.52 g (50 mmol) of bis(4-fluorophenyl)phenylphosphine sulfide and 1.70 g (50 mmol) of hydrogen peroxide (4.3 ml of a 35% aqueous solution).

Melting point: 126° C.

Example 6

The procedure was as in Example 2. 13.5 g (97% of theory) of triphenylphosphine oxide were obtained from 14.72 g (50 mmol) of triphenylphosphine sulfide and 1.70 g (50 mmol) of hydrogen peroxide (4.3 ml of a 35% solution).

Melting point: 154° C.

Example 7

13.41 g (50 mmol) of bis(4-fluorophenyl)methylphosphine sulfide were dissolved in 50 ml of propionic acid at 50° C., and 1.79 g (52.5 mmol) of hydrogen peroxide (4.51 ml of an 11.63 molar aqueous solution) were added dropwise at 50° C., with ice cooling. After 30 minutes at 50° C., the mixture was cooled to 20° C., and filtered and the solvent was distilled off at 100° C./20 mbar. The residue was suspended in water and treated with 2N NaOH until an alkaline reaction was obtained, and bis(4-chlorophenyl)phenylphosphine oxide was filtered off, rinsed with water and dried at 100° C./20 mbar.

Yield: 16.4 g (94% of theory);
Melting point: 107° C.

Example 8

7.26 g (20 mmol) of bis(4-chlorophenyl)phenylphosphine sulfide were suspended in 25 ml of acetic anhydride at 50° C., and 0.72 g (21.2 mmol) (1.81 ml of a 35% solution) of hydrogen peroxide was added dropwise, with cooling. After 30 minutes at 50° C., the mixture was cooled to room temperature and filtered, the filtrate was concentrated on a rotary evaporator and the residue was stirred with 25 ml of water. 2N NaOH was added until an alkaline reaction was obtained, the solid was filtered off and the filtrate was distilled.

Yield: 6.2 g (89% of theory).

Example 9

7.26 g (20 mmol) of bis(4-chlorophenyl)phenylphosphine sulfide, dissolved in 12.5 ml of glacial acetic acid/12.5 ml of toluene, and 0.72 g (21.1 mmol) (1.81 ml of a 35% solution) of hydrogen peroxide gave 6.4 g (92% of theory) of bis(4-chlorophenyl)phenylphosphine oxide after a reaction time of 60 minutes at 50° C. and working-up as in Example 8.

(B) COMPARISON EXAMPLES 20 mmol of each of the appropriate phosphine sulfides were dissolved or suspended in 20 ml of the solvents indicated below (a, b=according to the invention; c, d, e=comparison) and 0.79 g of hydrogen peroxide (23.2 mmol=2 ml of a 35% solution) was added at 50° C. In the cases where carboxylic acids were used as the solvent (examples according to the invention), a spontaneous reaction took place with an increase in temperature. With the other solvents listed (comparison examples), an exothermic reaction was not observed.

A sample was taken every 30 minutes at 50° C. (or every 1–2 hours in the case of longer reaction times) and tested by thin layer chromatography for the presence of residual phosphine sulfide. The table shows the times required until phosphine sulfide was no longer detectable:

| Solvent | Phosphine sulfide | | |
|---|---|---|---|
| | $CH_3-\overset{\overset{S}{\|}}{P}-(\text{C}_6\text{H}_4-F)_2$ | $(\text{C}_6\text{H}_5-)_3\overset{\overset{S}{\|}}{P}$ | $(Cl-\text{C}_6\text{H}_4-)_2\overset{\overset{S}{\|}}{P}-\text{C}_6\text{H}_5$ |
| (a) Glacial acetic acid | 30 minutes | 30 minutes | 30 minutes |
| (b) Propionic acid | 1 h | 1 h | 1 h |
| (c) Methanol | 16 h | 16 h | 12 h |
| (d) Acetonitrile | 12 h | 8 h | 16 h |
| (e) Acetone | 8 days+ | 8 days+ | 8 days+ |

[1] at 30° C. (incomplete reaction)

I claim:

1. An improved process for the preparation of tertiary phosphine oxides by oxidizing tertiary phosphine sulfides with hydrogen peroxide in a solvent, wherein the improvement comprises using a solvent containing at least about 20% by weight of optionally halogenated, lower aliphatic carboxylic acids, their anhydrides or mixtures thereof, the remainder of the solvent being composed of other inert miscible solvents.

2. The process as claimed in claim 1, wherein the solvent consists of optionally halogenated, aliphatic $C_1$-$C_6$-carboxylic acids, their anhydrides or mixtures thereof.

3. The process as claimed in claim 1, wherein the tertiary phosphine sulfides used are compounds of the formula

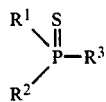

wherein $R^1$, $R^2$ and $R^3$ are, independently of one another, $C_1$-$C_{12}$-alkyl, $C_6$-$C_{10}$-aryl or $C_6$-$C_{20}$-aralkyl groups unsubstituted or substituted by halogen atoms.

4. The process as claimed in claim 1, wherein the hydrogen peroxide is used in approximately an equimolar quantity based on the starting phosphine sulfide.

5. The process as claimed in claim 1, wherein the oxidation is carried out at a temperature of between about −5° and 100° C.

6. The process as claimed in claim 1, wherein the solvent contains at least about 50% by weight of optionally halogenated, lower aliphatic carboxylic acids, their anhydrides or mixtures thereof.

7. The process as claimed in claim 1, wherein the tertiary phosphine sulfides used are compounds of the formula

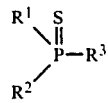

wherein $R^1$, $R^2$ and $R^3$ are, independently of one another, $C_6$-$C_{10}$-aryl or $C_6$-$C_{20}$-aralkyl groups unsubstituted or substituted by alkyl radicals.

8. The process as claimed in claim 2, wherein the solvent is acetic acid.

9. The process as claimed in claim 2, wherein the aliphatic $C_1$-$C_6$ carboxylic acids or their anhydrides are halogenated with fluorine or chlorine.

10. The process as claimed in claim 3, wherein the $R^1$, $R^2$ and $R^3$ groups are substituted by fluorine or chlorine.

11. The process as claimed in claim 4, wherein the hydrogen peroxide used is an aqueous concentration of approximately 30 to 35%.

12. The process as claimed in claim 5, wherein the oxidation is carried out at a temperature of between about 40° and 80° C.

13. The process as claimed in claim 7, wherein the $R^1$, $R^2$ and $R^3$ groups are substituted by alkyl radicals having up to four carbon atoms.

14. The process as claimed in claim 12, wherein the reaction is carried out for a time of about 30 minutes.

* * * * *

UNITED STATES PATENT AND TRADEMARK OFFICE
CERTIFICATE OF CORRECTION

PATENT NO. : 4,675,446

DATED : June 23, 1987

INVENTOR(S) : Erwin Weiss

It is certified that error appears in the above-identified patent and that said Letters Patent is hereby corrected as shown below:

Column 6, line 13, "13.41 g (50 mmol) of bis(4-fluorophenyl)methylphos-" should read --18.16 g (50 mmol) of bis(4-chlorophenyl)phenylphos- --.

Signed and Sealed this

Twenty-third Day of May, 1989

Attest:

DONALD J. QUIGG

Attesting Officer    Commissioner of Patents and Trademarks